(12) United States Patent
Wilmet et al.

(10) Patent No.: US 7,067,706 B2
(45) Date of Patent: *Jun. 27, 2006

(54) METHOD FOR PREPARING A HYDRO(CHLORO)FLUOROALKANE AND CATALYST

(75) Inventors: Vincent Wilmet, Wavre (BE); Francine Janssens, Vilvoorde (BE)

(73) Assignee: Solvay (Societe Anonyme) (BE)

( * ) Notice: Subject to any disclaimer, the term of this patent is extended or adjusted under 35 U.S.C. 154(b) by 292 days.

This patent is subject to a terminal disclaimer.

(21) Appl. No.: 10/257,590

(22) PCT Filed: Apr. 9, 2001

(86) PCT No.: PCT/EP01/04098

§ 371 (c)(1),
(2), (4) Date: Nov. 25, 2002

(87) PCT Pub. No.: WO01/77048

PCT Pub. Date: Oct. 18, 2001

(65) Prior Publication Data

US 2004/0024271 A1 Feb. 5, 2004

(30) Foreign Application Priority Data

Apr. 12, 2000 (FR) .................................. 00/04794

(51) Int. Cl.
C07C 17/00 (2006.01)
B01J 23/00 (2006.01)

(52) U.S. Cl. .................. 570/164; 570/168; 570/169; 502/305; 502/306; 502/313

(58) Field of Classification Search ................ 570/164, 570/168, 169; 502/305, 306, 313
See application file for complete search history.

(56) References Cited

U.S. PATENT DOCUMENTS

| | | | |
|---|---|---|---|
| 3,755,477 A | 8/1973 | Firth et al. | 260/653.4 |
| 4,547,483 A | 10/1985 | Müller et al. | 502/226 |
| 4,843,181 A * | 6/1989 | Gumprecht et al. | 570/169 |
| 5,155,082 A * | 10/1992 | Tung et al. | 502/228 |
| 5,545,298 A | 8/1996 | Braun et al. | 204/157.6 |
| 5,629,461 A * | 5/1997 | Yasuhara et al. | 570/168 |
| 5,932,776 A | 8/1999 | Cheminal et al. | 570/168 |
| 6,433,233 B1 | 8/2002 | Kanemura et al. | 570/165 |
| 6,841,706 B1 | 1/2005 | Wilmet et al. | |

FOREIGN PATENT DOCUMENTS

| | | |
|---|---|---|
| DE | 2 032 098 | 6/1970 |
| EP | 0 130 532 | 10/1985 |
| EP | 0 609 123 | 8/1994 |
| EP | 0 641 598 | 3/1995 |
| EP | 0 675 409 | 6/1995 |
| EP | 0 773 061 | 5/1997 |
| EP | 0 801 980 | 10/1997 |
| EP | 0 847 801 | 6/1998 |
| EP | 0 957 074 | 11/1999 |
| EP | 1 038 858 | 9/2000 |
| JP | 2 172 932 | 4/1990 |
| JP | 2 178 237 | 11/1990 |
| WO | 99/31032 | 6/1999 |
| WO | 00/21660 | 4/2000 |

OTHER PUBLICATIONS

6001 Chemical Abstracts, Columbus, Ohio, vol. 97, No. 11, Sep. 13, 1982.

* cited by examiner

Primary Examiner—Sikarl A. Witherspoon
(74) Attorney, Agent, or Firm—Connolly Bove Lodge & Hutz

(57) ABSTRACT

Process for the preparation of a hydro(chloro)fluoroalkane according to which a halogenated precursor of the hydro (chloro)fluoroalkane is reacted with hydrogen fluoride in the presence of a catalyst comprising chromium (Cr) and at least one other metal selected from the group consisting of aluminium, barium, bismuth, calcium, cerium, copper, iron, magnesium, strontium, vanadium and zirconium.

16 Claims, No Drawings

METHOD FOR PREPARING A HYDRO(CHLORO)FLUOROALKANE AND CATALYST

This application is the national stage of PCT/EP01/0498 filed Apr. 9, 2001 and published as WO01/77048 on Oct. 18, 2001.

The present invention relates to a process for the preparation of a hydro(chloro)fluoroalkane and a catalyst.

When a halogenated precursor of a hydro(chloro)fluoroalkane is reacted in the presence of hydrogen fluoride under fluorination conditions, it is difficult to selectively obtain a desired hydro(chloro)fluoroalkane. The formation of other reaction products, which often cannot be recycled or used, such as undesired isomers or dismutation products, reduces the productive output of hydro(chloro)fluoroalkane.

It is, for example, known from JP-A-02/178237 to carry out a hydrofluorination of perchloroethylene with hydrogen fluoride in the presence of a catalyst comprising chromium, magnesium and aluminium oxides. This process has an unsatisfactory productive output of pentafluoroethane (HFC-125). The process is not more satisfactory with regard to the selectivity for 1,1,1-trifluoro-2,2-dichloroethane (HCFC-123).

It was therefore desirable to find a process which would make possible access in a controlled and selective manner to a specific hydro(chloro)-fluoroalkane.

The invention consequently relates to a process for the preparation of a hydro(chloro)fluoroalkane according to which a halogenated precursor of the hydro(chloro)fluoroalkane is reacted with hydrogen fluoride in the presence of a catalyst comprising chromium (Cr) and at least one other metal (M) selected from aluminium, barium, bismuth, calcium, cerium, copper, iron, magnesium, strontium, vanadium and zirconium, in which process the catalyst is depleted in ammonium ions.

It has been found, surprisingly, that the process according to the invention makes possible access with high selectivity to a specific hydro(chloro)-fluoroalkane with high overall selectivity for hydro(chloro)fluoroalkane and for hydrochlorofluorinated precursors of the said hydro(chloro)fluoroalkane.

In the process according to the invention, the catalyst typically includes at most 1% by weight of ammonium ions. It preferably exhibits a content of ammonium ions of at most 0.5% by weight. The content of ammonium ions in the catalyst is preferably at most 0.2% by weight. Excellent results are obtained with a catalyst for which the content of ammonium ions is at most 0.1% by weight. Particularly advantageous results are obtained with a catalyst for which the content of ammonium ions is at most 0.05% by weight.

The catalyst can be a bulk or supported catalyst. A bulk catalyst is preferred.

The M/Cr atomic ratio of the metal M to the chromium in the catalyst is generally at least 0.01. The atomic ratio is preferably at least 0.05, advantageously at least 0.1. The atomic ratio is generally at most 100. It is most often at most 20. It is preferably at most 10.

The catalyst generally exhibits a specific surface determined according to the BET method with nitrogen, of at least 15 $m^2/g$, preferably of at least 25 $m^2/g$. The specific surface is generally at most 200 $m^2/g$. It is preferably at most 100 $m^2/g$.

In the process according to the invention, the catalyst is preferably obtained by fluorination of a mixed oxide of chromium and of metal M. The fluorination is preferably carried out with hydrogen fluoride, optionally diluted with an inert gas, such as nitrogen or helium. The duration of the fluorination is generally from 1 to 100 h. The fluorination temperature is generally between 150 and 400° C. It is preferably at most 350° C. The fluorination can be carried out, for example, immediately before the reaction of the halogenated precursor with hydrogen fluoride, preferably in the reactor used for the latter reaction.

The preparation of the mixed oxide preferably comprises a stage of coprecipitation by reaction of an aqueous solution of soluble metal and chromium salts, which is reacted an aqueous ammonia solution.

The preparation of the mixed oxide can advantageously comprise one or more drying or calcination stages. The temperature of the calcination is generally from 150° C. to 400° C. The calcination temperature is preferably at most 350° C. A calcination temperature of at most 340° C. is more particularly preferred. The calcination is often carried out at a temperature of at least 200° C.

After calcination, the mixed oxide generally exhibits a specific surface, determined according to the BET method with nitrogen, of at least 150 $m^2/g$, preferably of at least 180 $m^2/g$. The specific surface of the mixed oxide is generally at most 450 $m^2/g$.

The preparation of the catalyst generally comprises a treatment intended to reduce, preferably to essentially completely remove, the content of ammonium ions in the catalyst. This treatment can, for example, be at least one washing, preferably with water, or a heat treatment or a combination of these treatments. The effectiveness of the treatment intended to reduce the content of ammonium ions is generally confirmed by methods known per se. For example, Nessler's reagent can be used to analyse the content of ammonium ions. This treatment is preferably applied to the mixed oxide precursor of the catalyst, before subjecting it to the fluorination stage.

In a particularly preferred alternative form, the preparation of the catalyst comprises the following stages:

(a) a preparation of a mixed oxide of metal M and of chromium by coprecipitation from an aqueous solution of soluble metal and chromium salts, which is reacted with an aqueous ammonia solution;

(b) a washing of the mixed oxide, intended to reduce, preferably to essentially completely remove, the content of ammonium ions in the catalyst;

(c) a calcination of the washed mixed oxide;

(d) a fluorination treatment of the calcined mixed oxide.

The catalyst and the mixed oxide are generally essentially amorphous. They are preferably completely amorphous.

In the process according to the invention, the reaction between the hydrogen fluoride and the chlorinated precursor is usually carried out at a temperature of 150 to 450° C. The reaction is preferably carried out in the gas phase. The pressure of the reaction is usually from 0.5 to 30 bar. The molar ratio of the hydrogen fluoride to the halogen precursor is usually from 1 to 100. The residence time is usually from 1 to 1000 s.

Halogenated precursors which can be used in the process according to the invention are known. The halogenated precursor is preferably a chlorinated precursor. Mention may be made, by way of example, of dichloromethane, trichloromethane, trichloroethylene, perchloroethylene and pentachloroethane.

In an alternative form, the process according to the invention applies to the synthesis of a hydrochlorofluoroalkane. In this alternative form, the metal M is advantageously selected from barium, bismuth, copper, iron, magnesium and strontium. The metal is preferably selected from barium, bismuth, magnesium and strontium. This alternative form of the process according to the invention has proved to be advantageous for preparing chlorofluoromethane, chlorodifluoromethane, 2-chloro-1,1,1-trifluoroethane or 2,2-dichloro-1,1,1-trifluoroethane.

This alternative form has proved to be particularly advantageous for preparing 2,2-dichloro-1,1,1-trifluoroethane (HCFC-123). In this case, the halogenated precursor advantageously comprises at least one chlorinated organic compound selected from perchloroethylene, 1,1,2-trichloro-2-fluoroethylene, 1,1,2-trichloro-2,2-difluoroethane and 1,1,2,2-tetrachloro-2-fluoroethane. The chlorinated organic compound is preferably selected from 1,1,2-trichloro-2,2-difluoroethane and perchloroethylene.

In another alternative form, the process according to the invention applies to the synthesis of a hydrofluoroalkane. In this alternative form, the metal is advantageously selected from aluminum, calcium, cerium, vanadium and zirconium. Zirconium and aluminum are preferred. Aluminium is particularly preferred.

In order to reduce the cost of the catalyst in the process according to the invention, it is advantageous to use a catalyst with a high content of aluminium with respect to the more expensive chromium. It has been found that, in the process according to the invention, hydrofluoroalkanes can be synthesized in a particularly selective and economic manner when use is made of a catalyst comprising chromium and aluminium in an Al/Cr atomic ratio of at least 0.5. This ratio is preferably at least 1. In a particularly preferred way, this ratio is at least 2. The Al/Cr atomic ratio is advantageously at most 20. This ratio is preferably at most 10. In a particularly preferred way, it is at most 5.

This second alternative form has proved to be advantageous for preparing difluoromethane, 1,1,2-tetrafluoroethane or pentafluoroethane.

This alternative form has proved to be particularly advantageous for preparing pentafluoroethane. In this case, the halogenated precursor is advantageously perchloroethylene or 2,2-dichloro-1,1,1-trifluoroethane. The pressure in this case is advantageously at most 15 bar, preferably less than 10 bar. The pressure is advantageously at least 1 bar. A lower pressure makes possible an additional increase in the selectivity for pentafluoroethane whereas a higher pressure makes it possible to increase the overall productive output of the process.

The invention also relates to the mixed oxide and to the catalyst which are described above.

The examples given below are intended to illustrate the invention without, however, limiting it. In the examples, the degree of conversion of the halogenated precursor is the ratio, expressed as per cent, of, on the one hand, the amount employed minus the unconverted amount to, on the other had, the amount employed; the selectivity for hydro(chloro)fluoroalkane is the ratio, expressed as per cent, of the amount of hydro(chloro)fluoroalkane formed to the amount which would have been formed if all the halogenated precursor converted had generated hydro(chloro)fluoroalkane; the overall selectivity is the sum of the selectivity for the desired hydro(chloro)fluoroalkane of all the recoverable intermediates; the yield of hydro(chloro)fluoroalkane is the product of the degree of conversion and the selectivity for this hydro(chloro)fluoroalkane.

EXAMPLES 1–7

1.61 of an aqueous solution comprising 0.56 mol/l of nitrates of chromium and of other metal M and exhibiting the desired atomic ratio of the chromium to the metal M were prepared. 0.7 l of aqueous ammonia solution, exhibiting a concentration of $NH_4OH$ of 4 mol/l, was added to the solution with stirring at ambient temperature. The precipitate was centrifuged. The cake was washed several times with water at approximately 65° C. until at least 80% of the initial content of ammonium ions in the cake, confirmed using Nessler's reagent, had been removed. The washed cake was dried for 2 days at 105° C. The agglomerates obtained after drying were milled to produce grains with a size of less than 5 mm. The grains were subjected to calcination for a total period of 69 h while flushing with nitrogen. The temperature was maintained first at 215° C. and then at 330° C. The specific surface (SS) of the mixed oxide obtained is shown in Table 1. It was determined according to the BET method with nitrogen, measured on a Carlo Erba Sorptomatic® 1990 device after degassing the samples at ambient temperature for 12 h under a vacuum of $10^{-5}$ torr. The content of ammonium ions in the mixed oxide is also shown in Table 1.

The mixed oxide was introduced into a tubular reactor made of Hastelloy C. A fluorination treatment was carried out with hydrogen fluoride gas (10 g/h per 100 $cm^3$ of mixed oxide) mixed with nitrogen for 8 h at a temperature of 200 to 350° C. The specific surface (SS) of the catalysts which are obtained is shown in Table 1.

10 $cm^3$ of the catalyst and a hydrogen fluoride/perchloroethylene (PER) mixture in a molar ratio of 10 mol/mol were introduced into a tubular reactor with an internal diameter of 15 mm. The reaction pressure was maintained at 1 bar and the temperature at 350° C. The residence time was 12.5 seconds.

The results are collated in Table 1 below. It emerges therefrom that the process according to the invention makes it possible to obtain a high yield of HFC-125. The process gives a high overall selectivity at high degrees of conversion.

TABLE 1

| No | Metal | M/Cr atomic ratio | SS mixed oxide ($m^2/g$) | Mixed oxide $NH_4^+$ content (g/kg) | SS catalyst ($m^2g$) | Degree of conversion (%) | Overall selectivity (%) | HFC-125 yield (%) |
|---|---|---|---|---|---|---|---|---|
| 1 | Al | 10/90 | 299 | 0.05 | 155 | 97.5 | 89.8 | 61.0 |
| 2 | Al | 50/50 | 351 | 0.003 | 78 | 81.1 | 92.4 | 36.7 |
| 3 | Al | 70/30 | 343 | <0.002 | 68 | 89.3 | 94.4 | 48.0 |
| 4 | Al | 90/10 | 351 | 0.004 | 54 | 79.2 | 94.0 | 35.1 |
| 5 | Zr | 10/90 | 238 | <0.002 | 77 | 98.0 | 92.8 | 649 |
| 6 | V* | 10/90 | 254 | 0.007 | 106 | 95.0 | 91.3 | 61.1 |
| 7 | Ca | 10/10 | 291 | <0.002 | 26 | 76.0 | 88.7 | 42.6 |

*Vanadium (III) chloride was used in the preparation

The invention claimed is:

1. A process for the preparation of a hydro(chloro)fluoroalkane according to which a halogenated precursor of the hydro(chloro)fluoroalkane is reacted with hydrogen fluoride in the presence of a catalyst comprising chromium (Cr) and at least one other metal (M) selected from aluminium, barium, bismuth, calcium, cerium, copper, iron, magnesium, strontium, vanadium and zirconium, in which process the content of ammonium ions $NH_4^+$ in the catalyst is present and is at most 1% by weight.

2. A process according to claim 1, in which the content of ammonium ions in the catalyst is present and is in an amount at most 0.2% by weight.

3. A catalyst comprising chromium (Cr) and at least one other metal (M) selected from aluminium, barium, bismuth, calcium, cerium, copper, iron, magnesium, strontium, vanadium and zirconium, in which catalyst the content of ammonium ions $NH_4^+$ is present and is in an amount at most 1% by weight.

4. The catalyst according to claim 3, in which the content of ammonium ions $NH_4^+$ is at most 0.2% by weight.

5. A mixed oxide comprising chromium (Cr) and at least one other metal selected from aluminium, barium, bismuth, calcium, cerium, copper, iron, magnesium, strontium, vanadium and zirconium, in which mixed oxide the content of ammonium ions $NH_4^+$ present and is in an amount at most 1% by weight.

6. A mixed oxide according to claim 5, in which the content of ammonium ions $NH_4^+$ is at most 0.2% by weight.

7. The process according to claim 1, wherein the catalyst exhibits a specific surface, determined according to the BET method, of at least 15 $m^2/g$.

8. The process according to claim 1, wherein the catalyst was obtained by fluorination of a mixed oxide of chromium and of metal M.

9. The process according to claim 8, wherein the mixed oxide was obtained by coprecipitation by reaction of an aqueous solution of soluble metal and chromium salts, which is reacted with an aqueous ammonia solution.

10. The process according to claim 8, wherein the mixed oxide exhibits, before fluorination, a specific surface, determined according to the BET method, of at least 150 $m^2/g$.

11. The process according to claim 1, applied to the synthesis of a hydrofluoroalkane and hydrochlorofluoralkane.

12. The process according to claim 11, wherein the metal is selected from the group consisting of aluminium, calcium, cerium, vanadium and zirconium.

13. The process according to claim 12, wherein the metal is aluminium.

14. The process according to claim 13, wherein the Al/Cr atomic ratio is from 0.5 to 20.

15. The process according to claim 11, wherein the hydrofluoroalkane obtained is pentafluoroethane.

16. The process according to claim 1, in which the metal is selected from barium, bismuth, copper, iron, magnesium and strontium.

* * * * *